(12) United States Patent
Kent

(10) Patent No.: US 12,714,414 B2
(45) Date of Patent: Aug. 25, 2026

(54) METHODS AND DEVICES FOR SUTURE ANCHOR CONTINUOUS COMPRESSION

(71) Applicant: DePuy Synthes Products, Inc., Raynham, MA (US)

(72) Inventor: Todd Kent, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 425 days.

(21) Appl. No.: 18/342,479

(22) Filed: Jun. 27, 2023

(65) Prior Publication Data

US 2025/0000556 A1 Jan. 2, 2025

(51) Int. Cl.
*A61B 17/04* (2006.01)

(52) U.S. Cl.
CPC .. *A61B 17/0401* (2013.01); *A61B 2017/0453* (2013.01)

(58) Field of Classification Search
CPC ........ A61B 17/0401; A61B 2017/0403; A61B 2017/0408; A61B 2017/0414; A61B 2017/042; A61B 2017/0422; A61B 2017/0424; A61B 2017/0425; A61B 2017/0427; A61B 2017/0429; A61B 2017/043; A61B 2017/0432; A61B 2017/0437; A61B 2017/0438; A61B 2017/0445; A61B 2017/0446; A61B 2017/0448; A61B 2017/045; A61B 2017/0451; A61B 2017/0453; A61B 2017/0454; A61B 2017/0456; A61B 2017/0461; A61B 2017/0462
See application file for complete search history.

(56) References Cited

U.S. PATENT DOCUMENTS

| | | | |
|---|---|---|---|
| 5,152,298 A * | 10/1992 | Kreyenhagen ..... | A61B 17/0401 607/116 |
| 5,306,290 A | 4/1994 | Martins et al. | |
| 5,814,072 A | 9/1998 | Bonutti | |
| 7,029,490 B2 | 4/2006 | Grafton et al. | |
| 7,235,091 B2 | 6/2007 | Thornes | |
| 7,766,939 B2 | 8/2010 | Yeung et al. | |
| 8,398,678 B2 | 3/2013 | Baker et al. | |
| 8,460,379 B2 | 6/2013 | Albertorio et al. | |

(Continued)

FOREIGN PATENT DOCUMENTS

| | | |
|---|---|---|
| CN | 108186096 A | 6/2018 |
| EP | 3206607 B1 | 5/2018 |
| RU | 2461366 C1 | 9/2012 |

*Primary Examiner* — Dianne Dornbusch

(57) ABSTRACT

An implant for placing a first bone anchor within a first bone. The first bone anchor may include an outer body including an outer surface configured to engage the first bone, an opening configured to pass a suture therethrough, and an inner channel. The first bone anchor may include a resilient element being deformable between a first and second state. The first bone anchor may include a suture coupler disposed within the inner channel, configured to couple to the suture and engage to the resilient element such that a force on the suture coupler in a proximal direction results in deformation of the resilient element to the second state and proximal translation of the suture coupler in relation to the outer body and a release of the force results in a return of the resilient element to the first state and distal translation of the suture coupler.

20 Claims, 9 Drawing Sheets

(56) References Cited

U.S. PATENT DOCUMENTS 8,764,798 B2 7/2014 Housman
8,888,779 B2 11/2014 Senn et al.
8,986,347 B2 3/2015 Housman
D740,417 S 10/2015 Chavan
D740,418 S 10/2015 Chavan et al.
D740,419 S 10/2015 Chavan et al.
9,179,950 B2 11/2015 Zajac et al.
9,192,369 B2 11/2015 Bittenson
9,364,210 B2 6/2016 Gregoire et al.
9,421,049 B2 8/2016 Rogachefsky
9,737,347 B2 8/2017 Schlienger et al.
9,826,969 B2 11/2017 Larsen
9,931,150 B2 4/2018 Philippon et al.
9,943,304 B2 4/2018 Branthover et al.
10,136,884 B2 11/2018 Graul et al.
10,149,752 B2 12/2018 Dougherty et al.
10,206,670 B2 2/2019 Thornes
10,251,686 B2 4/2019 Zajac et al.
10,327,826 B2 6/2019 Horrell et al.
10,390,816 B2 8/2019 Thornes
10,413,341 B2 9/2019 Chaudot et al.
10,492,774 B2 12/2019 Larsen
10,499,900 B2 12/2019 Wade
10,646,215 B2 5/2020 Dooney et al.
10,695,049 B2 6/2020 Thornes
10,722,229 B2 7/2020 O'Donnell et al.
10,736,622 B2 8/2020 Thornes
10,864,028 B2 12/2020 Zajac et al.
10,918,375 B2 2/2021 Thornes
11,013,508 B2 5/2021 Arai et al.
11,109,855 B2 9/2021 Shoshtaev et al.
11,129,654 B2 9/2021 Zajac et al.
11,253,301 B2 2/2022 Larsen et al.
2005/0261709 A1* 11/2005 Sakamoto ........ A61B 17/12013 606/139
2007/0276437 A1* 11/2007 Call .................. A61B 17/0487 606/232
2008/0288070 A1* 11/2008 Lo ..................... A61B 17/0401 623/13.13
2012/0130492 A1* 5/2012 Eggli ................... A61F 2/0811 623/13.14
2013/0197578 A1* 8/2013 Gregoire ............ A61B 17/0401 606/232
2014/0081326 A1* 3/2014 Takahashi .......... A61B 17/0487 606/232
2016/0038186 A1 2/2016 Herzog
2016/0228117 A1* 8/2016 Borden .............. A61B 17/0401
2018/0049784 A1 2/2018 Gault et al.
2020/0281581 A1 9/2020 Triplett et al.
2021/0059729 A1 3/2021 Zajac et al.
2021/0161518 A1 6/2021 Thornes
2021/0219972 A1 7/2021 Zakhary
2022/0096235 A1* 3/2022 Giese .................... A61F 2/2457
2022/0142635 A1 5/2022 Bachmaier et al.
2022/0168092 A1 6/2022 Anderson
2022/0192817 A1 6/2022 Gill et al.

* cited by examiner

METHODS AND DEVICES FOR SUTURE ANCHOR CONTINUOUS COMPRESSION

FIELD

The present invention generally relates to methods and devices for suture anchor continuous compression. More specifically, certain embodiments relate to methods and devices for providing continuous compression in the fixation of two bones, or of a bone and surrounding soft tissue, following an injury.

BACKGROUND

Typical treatment for bone fixation or soft tissue repair, such as following a syndesmotic injury, involves stabilizing the two bones, or a bone to the surrounding soft tissue, in the proper orientation and holding them there throughout the soft tissue healing period to allow the ligaments to re-attach and heal. Oftentimes, this treatment involves the use of suture anchor repair to hold the bones and/or soft tissue in place.

Accordingly, alternative devices and methods for providing suture anchor continuous compression would be useful.

SUMMARY

The present invention is directed to methods and devices for providing continuous compression while stabilizing a joint between two bones, e.g., the tibia and fibula, or between soft tissue and a bone, during a healing period following a traumatic injury.

An example implant is provided for placing a first bone anchor within a first bone, such as the tibia. The first bone anchor may include an outer body including an outer surface configured to engage the first bone, an opening at a proximal end of the outer body configured to pass a suture therethrough, and an inner channel. The first bone anchor may further include a resilient element disposed within the inner channel of the outer body and being deformable between a first state and a second state. The first bone anchor may further include a suture coupler disposed within the inner channel of the outer body. The suture coupler may be configured to couple to the suture and engage to the resilient element. A force on the suture coupler in a proximal direction results in deformation of the resilient element to the second state. A proximal translation of the suture coupler in relation to the outer body and a release of the force results in a return of the resilient element to the first state and distal translation of the suture coupler.

The resilient element may be disposed in a proximal direction in relation to the suture coupler and may be configured to compress in response to the force in the proximal direction on the suture coupler.

The resilient element may be disposed in a distal direction in relation to the suture coupler and may be configured to elongate in response to the force in the proximal direction on the suture coupler.

The outer surface of the outer body may include screw threads.

The proximal end of the outer body may be shaped to receive a drive end of a suture anchor driver.

The implant may further include the suture, wherein tension on the suture may be configured to apply the force on the suture coupler in the proximal direction.

The implant may further include a second bone anchor configured to engage the suture, wherein the first and second bone anchors may be configured to engage one or more bones such that the suture extends orthogonally in relation to the first bone anchor.

The suture may be configured appose soft tissue.

The second bone anchor may include a threaded screw, a barbed fastener, a button, and/or a cap.

A first end of the resilient element may be prevented, by the outer body, from translating longitudinally in relation to the outer body. A second end of the resilient element may be engaged to the suture coupler. A length of the resilient element between the first end and the second end may be configured to deform in response to the force on the suture coupler.

The inner channel may include an internal notch configured to prevent the first end of the resilient element from moving proximally within the first bone anchor.

The resilient element may include rubber, polyurethane, and/or nitinol.

The resilient element may include a coil spring.

An example method is provided for bracing soft tissue. The method may include inserting a distal end of a first bone anchor into a first bone hole via a driver engaged to a proximal end of the first bone anchor. The method may further include extending a suture from the proximal end of the first bone anchor such that a length of the suture is configured to move into and out of an opening at the proximal end of the first bone anchor in response to variation in tension on the suture.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 80%" may refer to the range of values from 62% to 98%.

The example devices and methods of treatment described herein generally involve providing syndesmosis repair of two bones, such as the tibia and fibula bones, or of a bone and soft tissue (e.g., a ligament, muscle, or tendon) via continuous compression. That is, a resilient element, such as a coil spring, may be inserted within a suture anchor disposed within a bone to provide continuous compression during the healing of an injury. This configuration may help to not only prevent the implant from being too tight and causing stiffness, but to also provide enough tension to reduce the chance of tear to surrounding soft tissue.

Various example systems and methods are presented herein. Features from each example are combinable with other examples as understood by persons skilled in the pertinent art.

Figure 1:
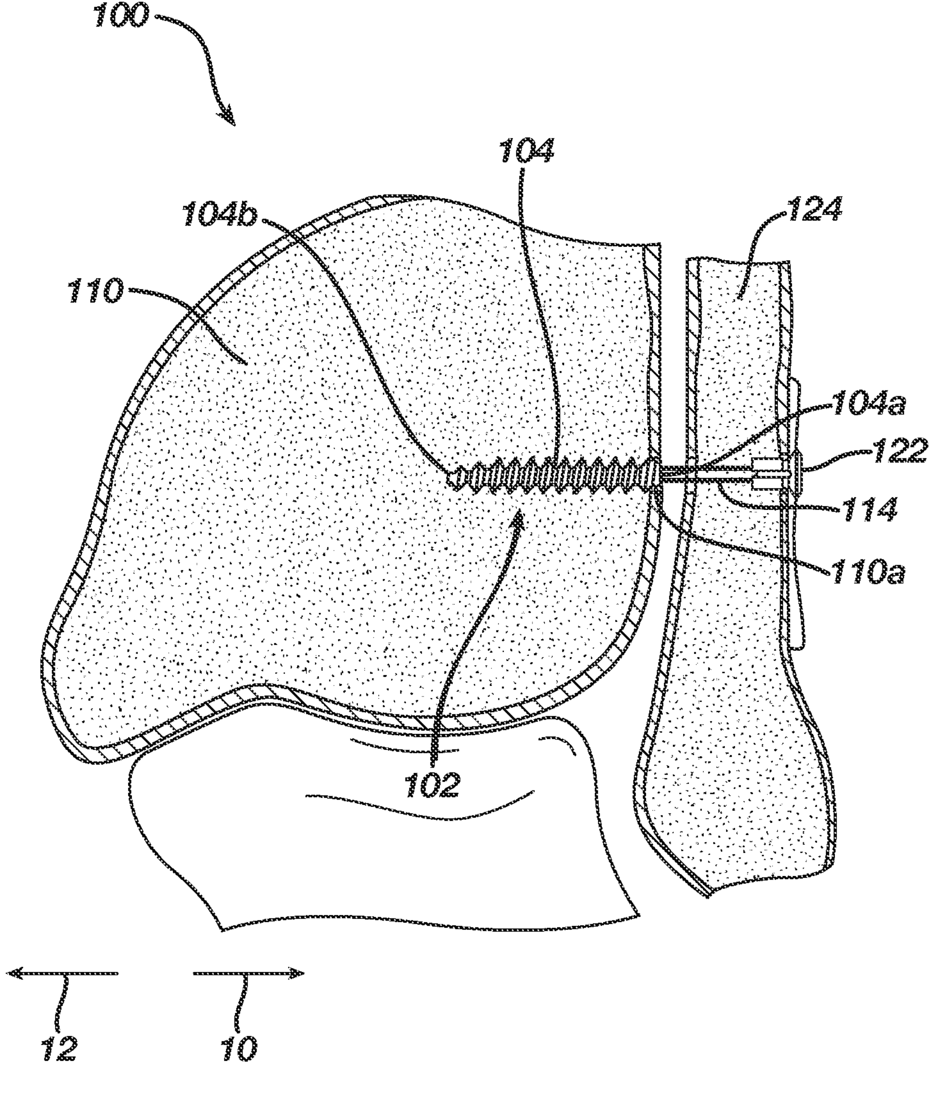
FIG. 1 is an illustration of an example system for suture anchor continuous compression according to aspects of the present invention.

FIG. 1 is an illustration of an example system 100 for a suture anchor applying continuous compression. The system 100 may include an implant 102 for the bracing of two bones, such as the tibia and fibula bones, or of a bone and surrounding soft tissue 128 (e.g., FIG. 2). The implant 102 may include a first bone anchor 104, which may include a proximal end 104*a* and a distal end 104*b*. The first bone anchor 104 may be configured to be inserted into a first bone 110 through a first bone hole 110*a*. In some embodiments, the implant 102 may further include a second bone anchor 122 configured to engage a second bone 124. The second bone anchor 122 may include a threaded screw, a barbed fastener, a button, and/or a cap.

The first and/or second bone anchors 104, 122 can include any type of suture anchor, and can be manufactured from a surgical stainless steel or other suitable biocompatible material, such as 316 LVM stainless steel, titanium, and other suitable materials, such as nitinol, bio-absorbables, or non-absorbables. First and/or second bone anchors 104, 122 can also include an "all-textile" anchor.

In some embodiments, the implant 102 may include a suture 114 configured to extend through the first bone anchor 104, as further discussed below. In some embodiments, the suture 114 may be configured to engage with the second bone anchor 122, such as one engaged with a second bone 124, the first bone anchor 104 only, and/or another first bone anchor 104.

The suture 114 can be manufactured out of a variety of fibers or filaments including but not limited to polymer filaments, metallic filaments, or organic filaments, or other filaments such as carbon fiber or carbon nanotubes, etc., and can be made of resorbable and/or biologic materials. Suture 114 can include, but is not limited to, a coreless suture, a suture with a jacket and a central core, a tape, or any other tension member available or contemplated, can be poly-coated or uncoated, and can include collagen.

Figure 2:
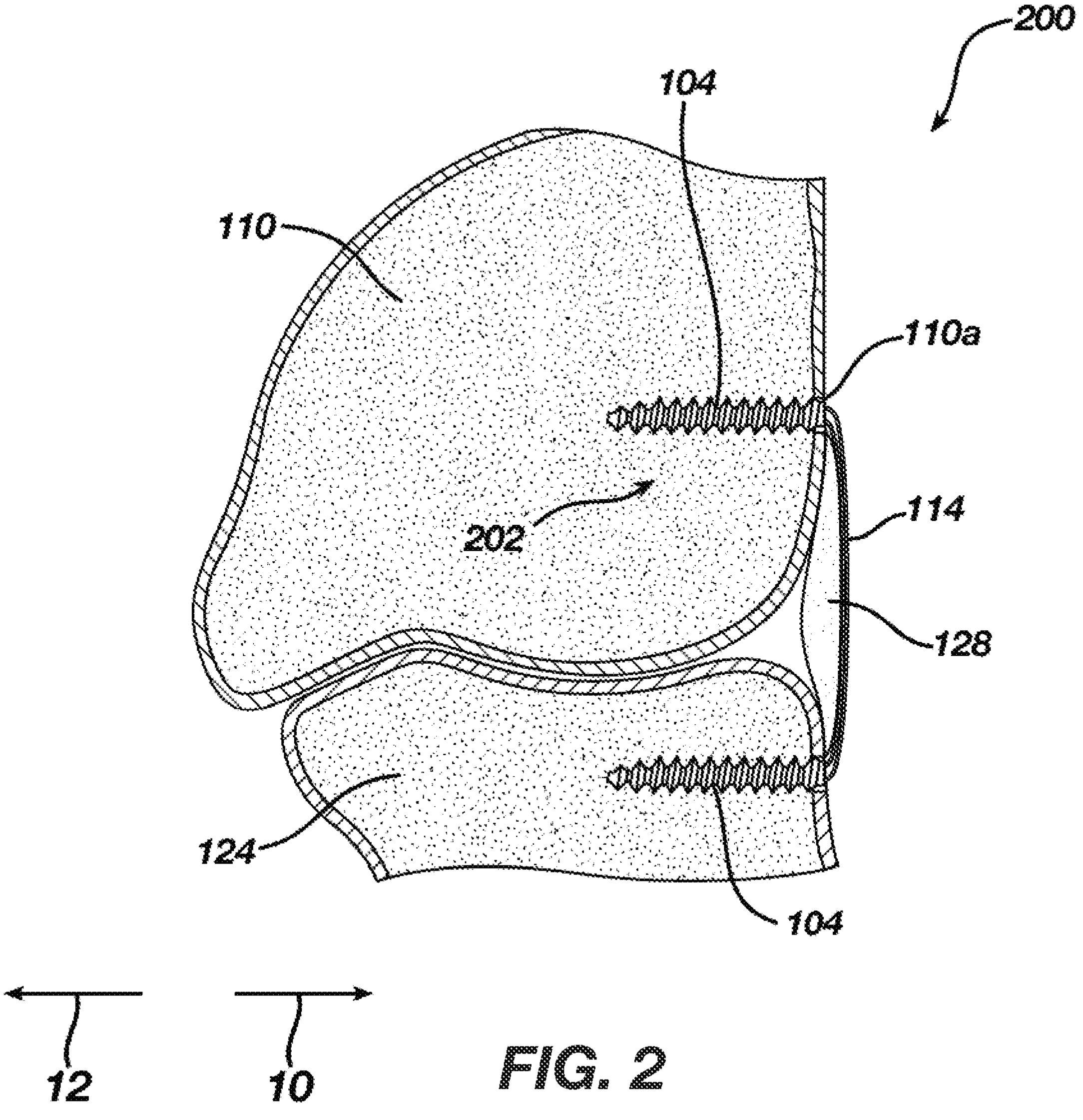
FIG. 2 is an illustration of another example system for suture anchor continuous compression according to aspects of the present invention.

FIG. 2 is an illustration of another example system 200 for suture anchor continuous compression. The system 200 may include an implant 202, and may be configured to provide bracing of two bones across a joint such that an included suture 114 may extend orthogonally in relation to a first bone anchor 104 in first bone 110 and a second first bone anchor 104 in second bone 124, and may be configured to appose soft tissue 128. In this example, the first and second bones 110, 124 may sit on top of one another, as opposed to in a linear configuration (e.g., as in FIG. 1).

Figure 3A:
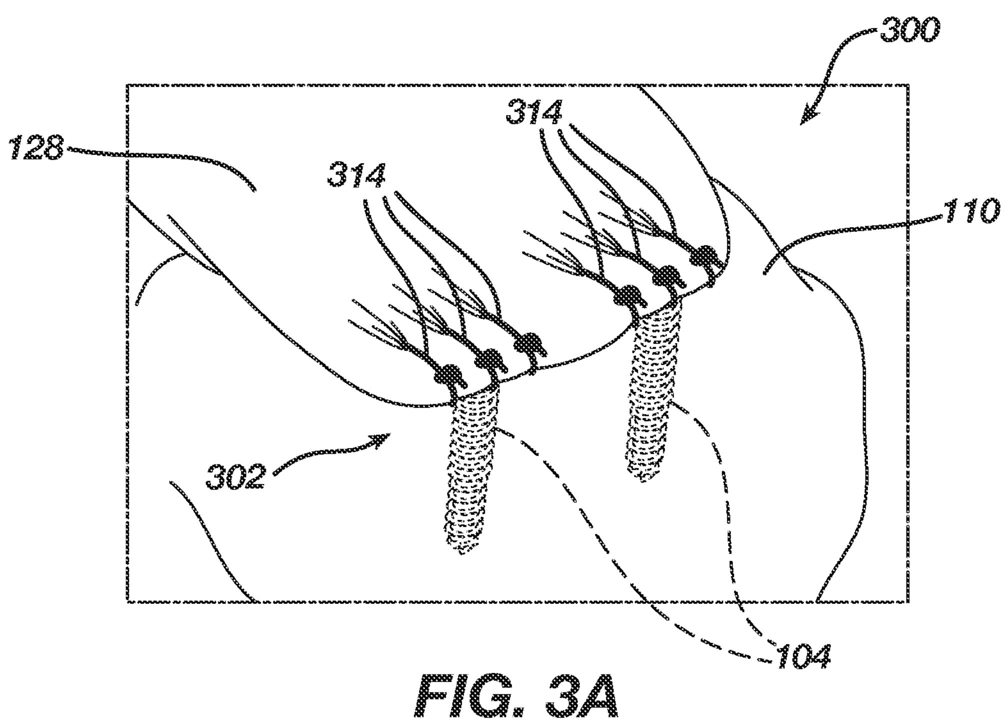
FIG. 3A is an illustration of another example system for suture anchor continuous compression according to aspects of the present invention.

As discussed above, FIG. 3A is an illustration of another example system 300 for suture anchor continuous compression, where the implant 302 may include one or more first bone anchors 104, and one or more sutures 314, where the suture(s) 314 are configured to engage with themselves and/or the first bone anchor 104 to provide bracing of a first bone 110 and surrounding soft tissue 128. In some embodiments, the suture(s) 314 may be configured to extend out of the distal end of the first bone anchor 104, to be stitched through the soft tissue 128, and be tied down to remain in place.

Figure 3B:
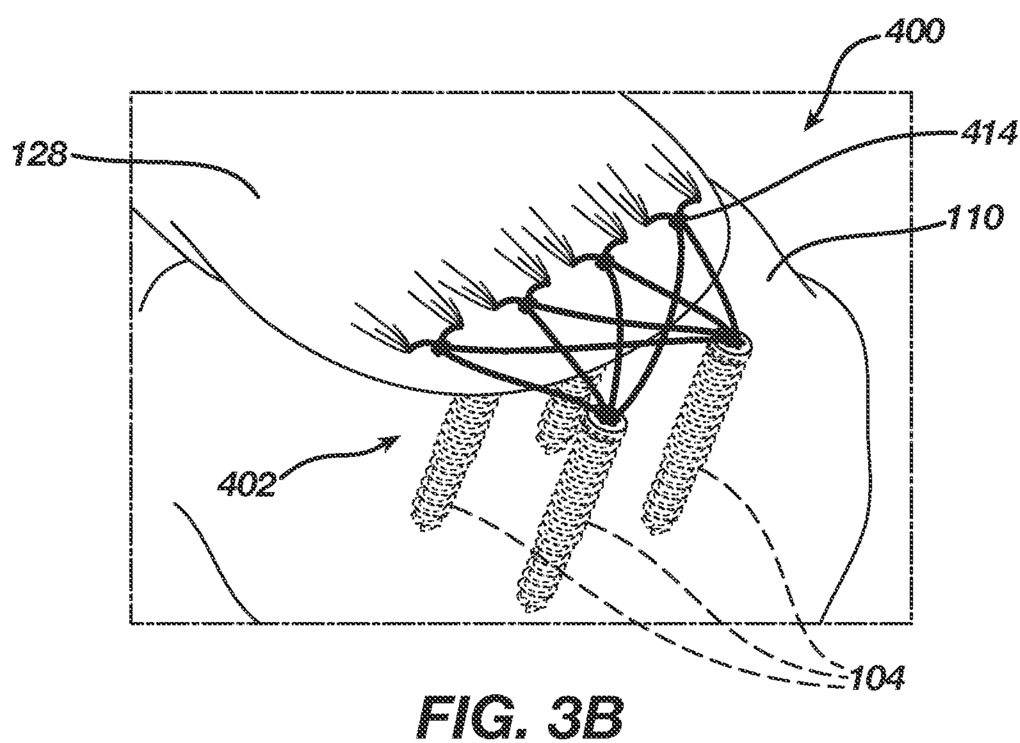
FIG. 3B is an illustration of another example system for suture anchor continuous compression according to aspects of the present invention.

As discussed above, FIG. 3B is an illustration of another example system 400 for suture anchor continuous compression, where the implant 402 may include one or more first bone anchors 104, and a suture(s) 414 configured to engage with itself, and one or more first bone anchors 104 to provide bracing of a first bone 110 and surrounding soft tissue 128. In some embodiments, one or more of the first bone anchors 104 may be placed more proximally under the soft tissue 128, while another one or more of the first bone anchors 104 may be placed more distally within the first bone 110 relative to the soft tissue 128. The suture(s) 414 may then be linked between these proximal and distal first bone anchors 104.

Figure 4A:
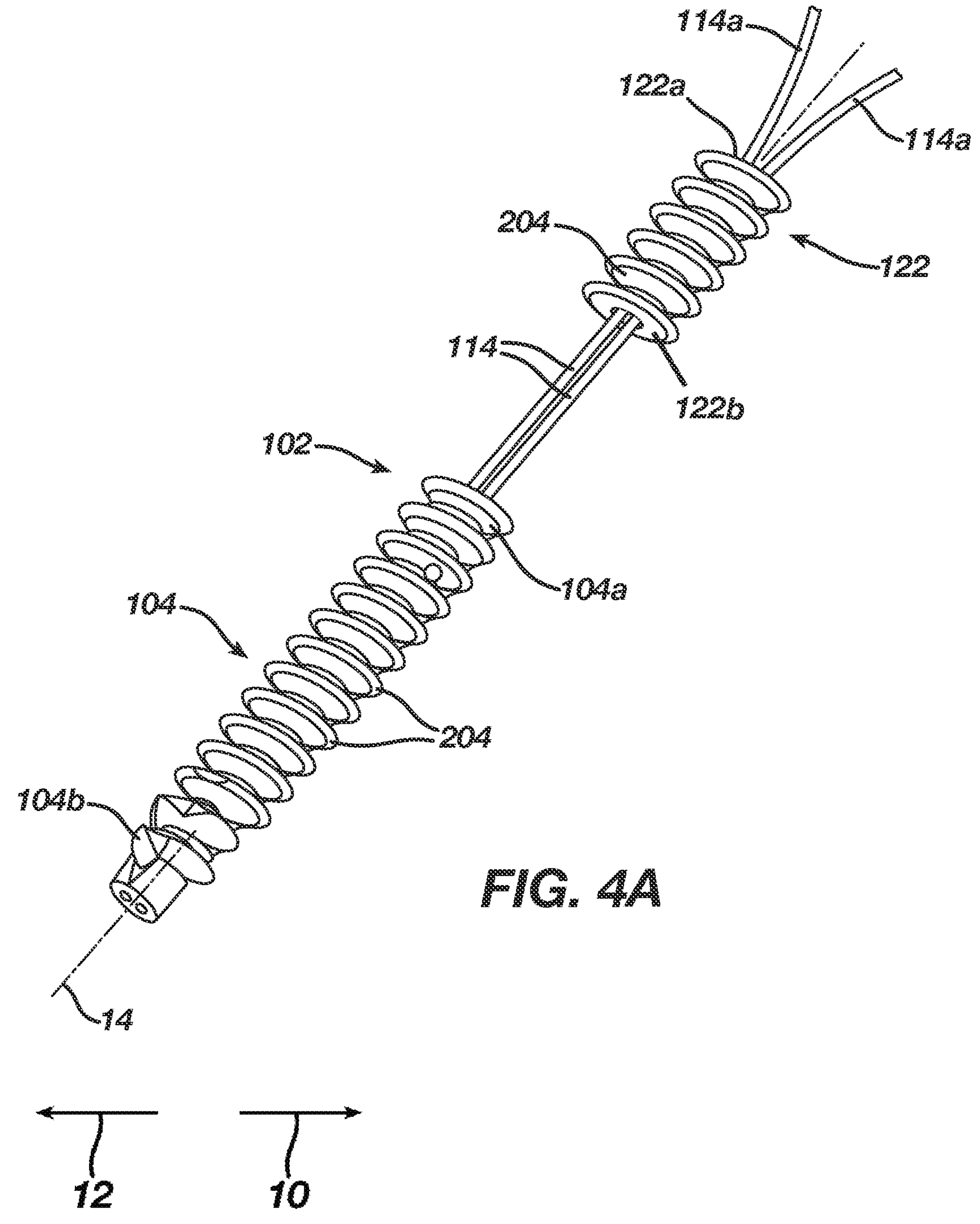
FIG. 4A is a perspective view of an example implant used for continuous compression and fixation between two bones according to aspects of the present invention.

In some embodiments, as particularly shown in FIG. 4A, implant 102 may include first bone anchor 104 and second bone anchor 122, each including one or more screw threads 204. The screw threads 204 of first bone anchor 104 and/or second bone anchor 122 may extend from the respective proximal end 104*a*, 122*a* helically towards the respective distal end 104*b*, 122*b*. With respect to the first bone anchor 104 and/or second bone anchor 122, the screw threads 204 may have a substantially uniform configuration along the threaded region, or the screw threads 204 may be varied as desired, e.g., having different heights, edges, and/or axial spacing, as desired. Additionally, the screw threads 204 can differ on each bone anchor 104, 122, or each bone anchor 104, 122 can be uniform but different from the other.

Figure 4B:
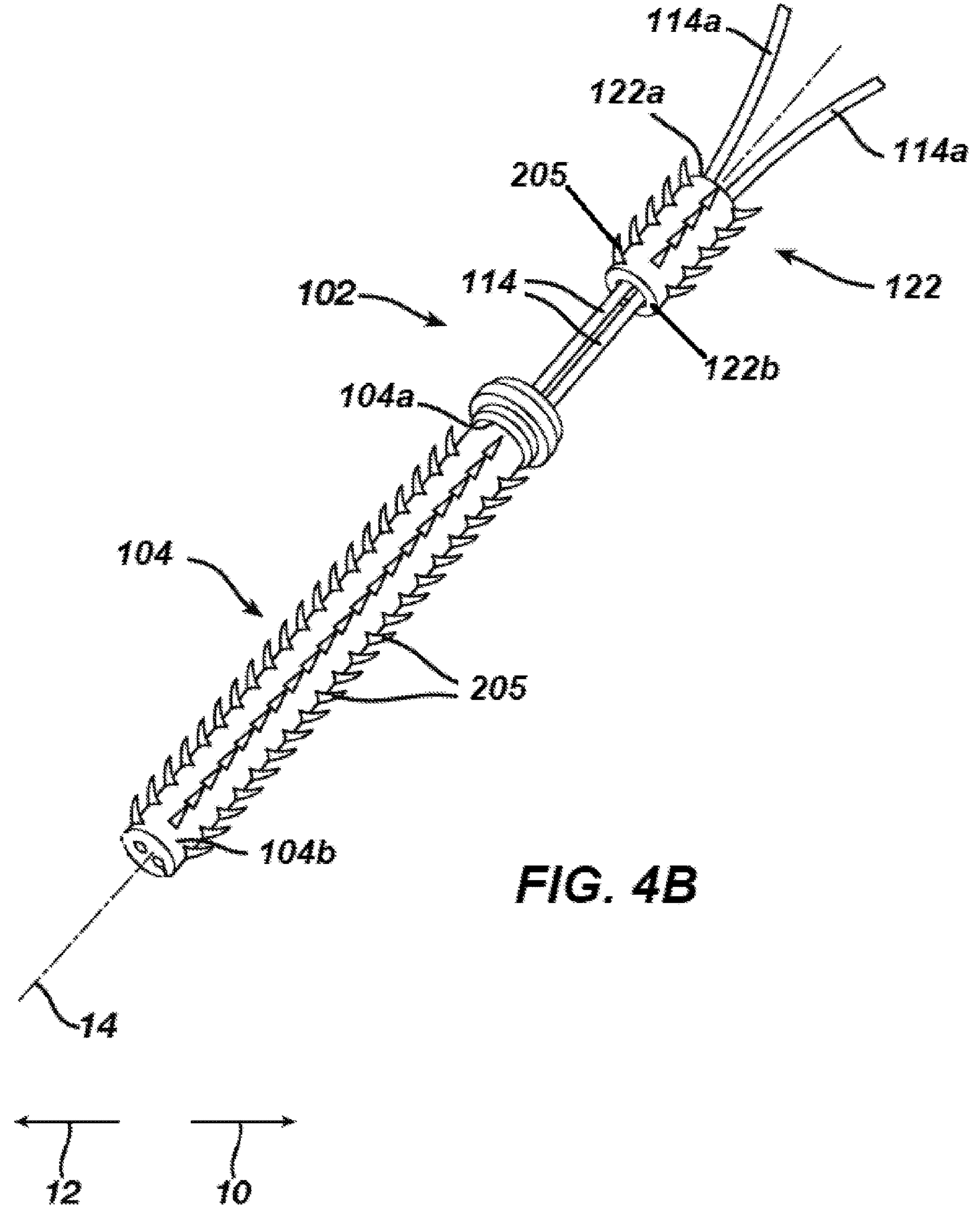
FIG. 4B is a perspective view of an example implant used for continuous compression and fixation between two bones according to aspects of the present invention.

In some embodiments, as particularly shown in FIG. 4B, implant 102 may include first bone anchor 104 and second bone anchor 122, each including one or more barbed ribs 205 that may extend from the respective proximal end 104*a*, 122*a* towards the respective distal end 104*b*, 122*b*, and in a repeating distally downward angled pattern. The barbed ribs 205 may have a substantially uniform configuration along the barbed region, or the barbed ribs 205 may be varied as desired, e.g., having different lengths, angles, and/or spacing, as desired.

One skilled in the pertinent art will appreciate that, aside from the disclosed examples, the first bone anchor 104 and second bone anchor 122 may include any style of bone anchor.

In some embodiments, suture 114 may be configured to extend through first bone anchor 104 and through second bone anchor 122 along the longitudinal axis 14. The proximal end(s) 114*a* of the suture 114 may be configured to extend past both the proximal end 104*a* of first bone anchor 104, and the proximal end 122*a* of second bone anchor 122.

Figures 5A, 5B:
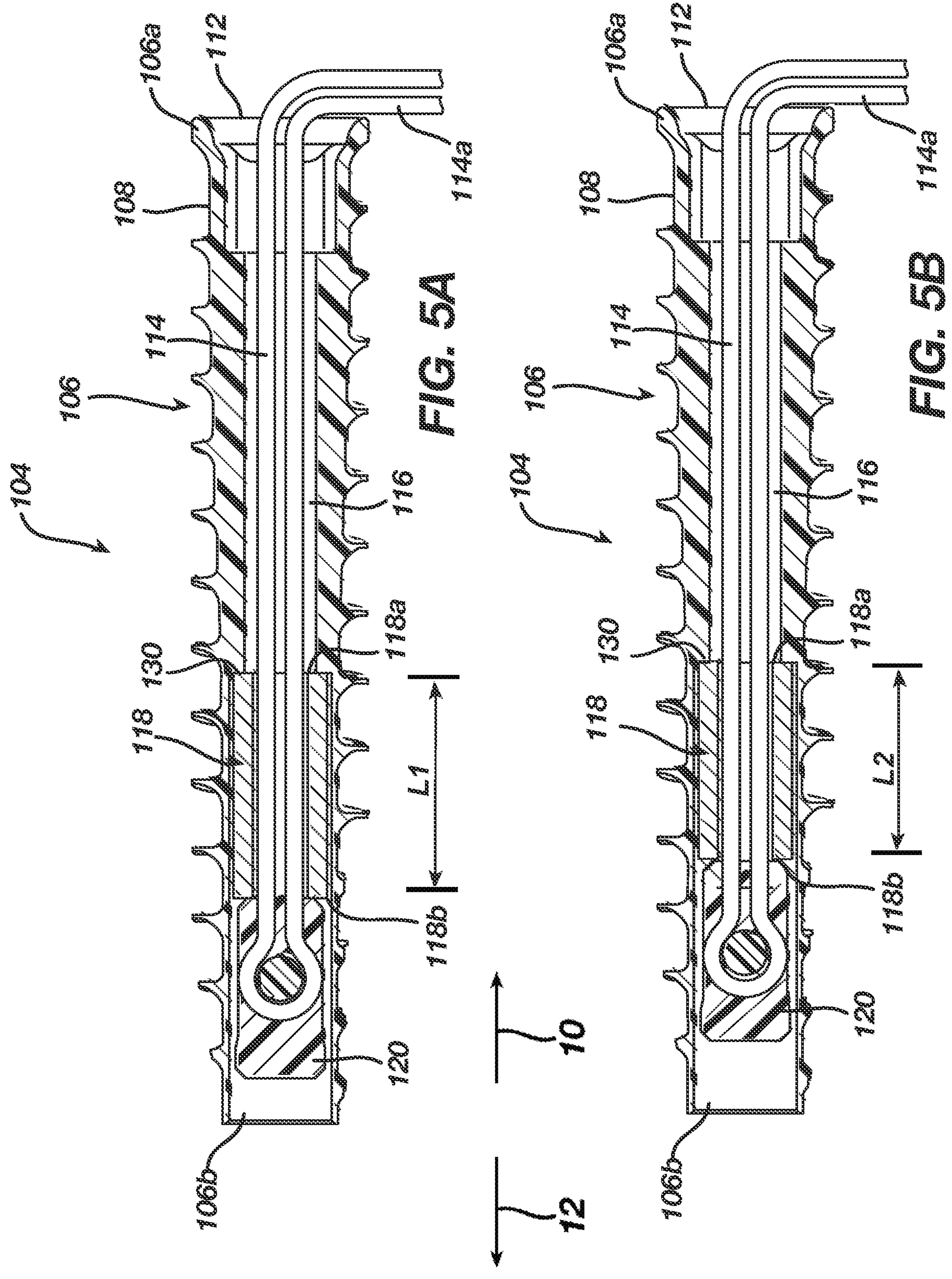
FIG. 5A is a cross-sectional view of an example first bone anchor for continuous compression and fixation between bones and/or soft tissue, the first bone anchor in a first state, according to aspects of the present invention.
FIG. 5B is a cross-sectional view of the example first bone anchor in FIG. 5A in a second state, according to aspects of the present invention.
Figure 6:
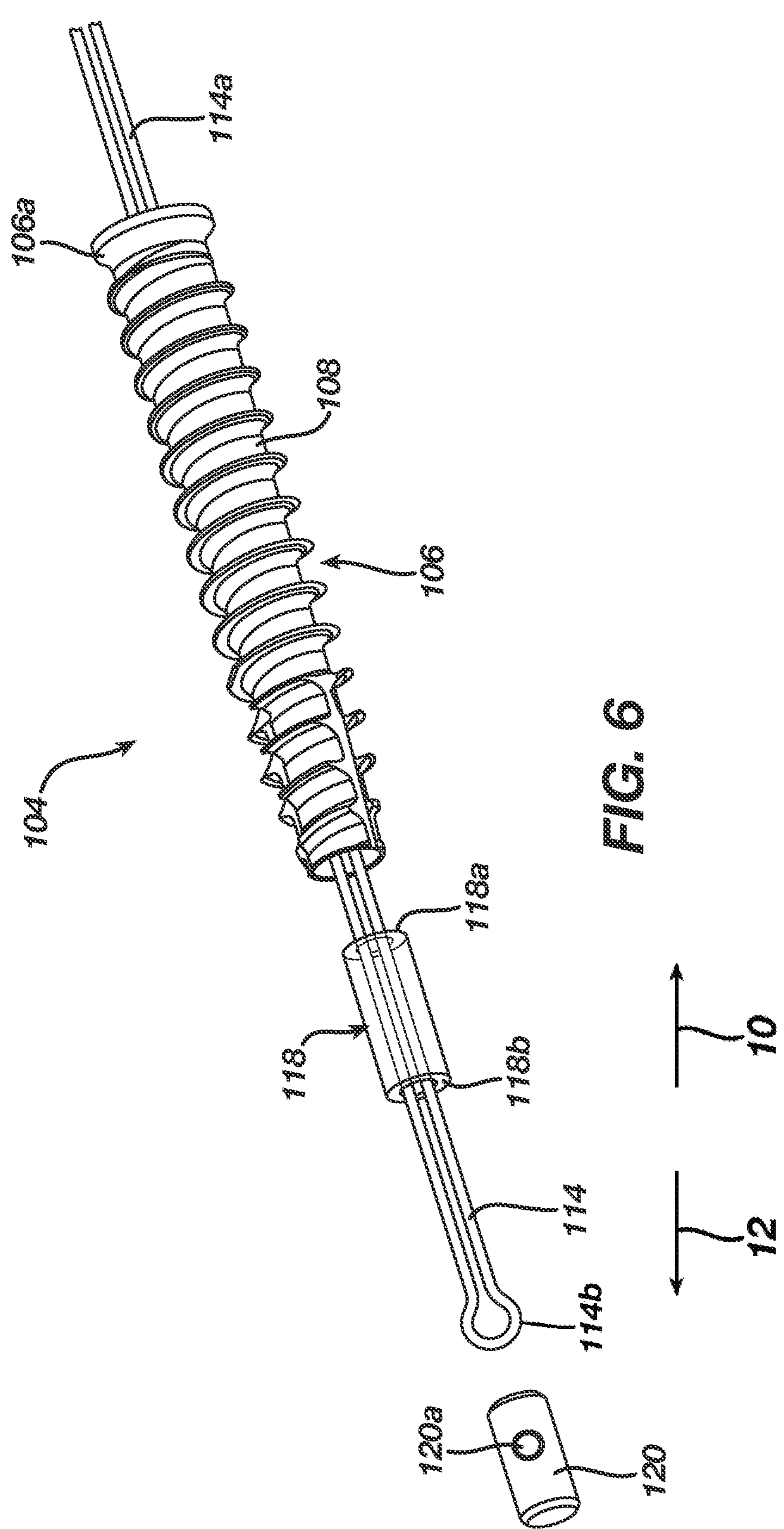
FIG. 6 is an exploded view of the example first bone anchor of FIG. 5A according to aspects of the present invention.

In some embodiments, as particularly shown in FIGS. 5A, 5B, and 6, first bone anchor 104 may include an outer body 106 including an outer surface 108 configured to engage the first bone 110, an opening 112 at a proximal end 106*a* of the outer body 106 configured to pass a suture 114 therethrough, and an inner channel 116. In some embodiments, as particularly shown in FIG. 4A, the outer surface 108 of the outer body 106 may include screw threads 204. In some embodiments, the outer surface 108 of the outer body 106 may be shaped to receive a drive end of a suture anchor driver for inserting the first bone anchor 104 into the first bone 110, as discussed further below.

The first bone anchor 104 may further include a resilient element 118 disposed within the inner channel 116 of the outer body 106. The resilient element 118 may be deformable between a first state and a second state, as further discussed below.

In some embodiments, as particularly shown in FIGS. 5A and 5B, the resilient element 118 may be disposed in a proximal direction 10 in relation to the suture coupler 120, and the resilient element 118 may be configured to compress in response to the force in the proximal direction 10 on the suture coupler 120. A first end 118*a* of the resilient element 118 may be prevented, by the outer body 106, from translating longitudinally in relation to the outer body 106. A second end 118*b* of the resilient element 118 may be engaged to the suture coupler 120.

In some embodiments, as particularly shown in FIGS. 5A and 5B and further discussed below, a length L1 (FIG. 5A) or L2 (FIG. 5B) of the resilient element 118 may be between the first end 118*a* and the second end 118*b* and may be configured to deform in response to the force on the suture coupler 120.

In some embodiments, as particularly shown in FIG. 6, a distal end 114*b* of the suture 114 may be configured in a looped or knotted configuration such that the suture 114 may not be pulled proximally through the first bone anchor 104.

In some embodiments, the first bone anchor 104 may include a suture coupler 120 disposed within the inner channel 116 of the outer body 106. The suture coupler 120 may be configured to couple to the suture 114, and to engage to the resilient element 118. As shown in FIG. 5B, a force on the suture coupler 120 in a proximal direction 10 (e.g., by pulling on suture 114), results in deformation of the resilient element 118 to the second state, where the resilient element 118 has a length L2. As shown in FIG. 5A, proximal translation of the suture coupler 120 in relation to the outer body 106 and a release of the force results in a return of the resilient element 118 to the first state, where the resilient element 118 has a length L1, and distal translation of the suture coupler 120. In some embodiments, as shown in FIGS. 5A and 5B, uncompressed length L1 of resilient element 118 while in the first state (FIG. 5A) is longer than a compressed length L2 of resilient element 118 while in the second state (FIG. 5B). In some embodiments, as particularly shown in FIGS. 5A and 5B, the inner channel 116 may include an internal notch 130 configured to prevent the first end 118*a* of the resilient element 118 from moving proximally within the first bone anchor 104.

Figures 7A, 7B:
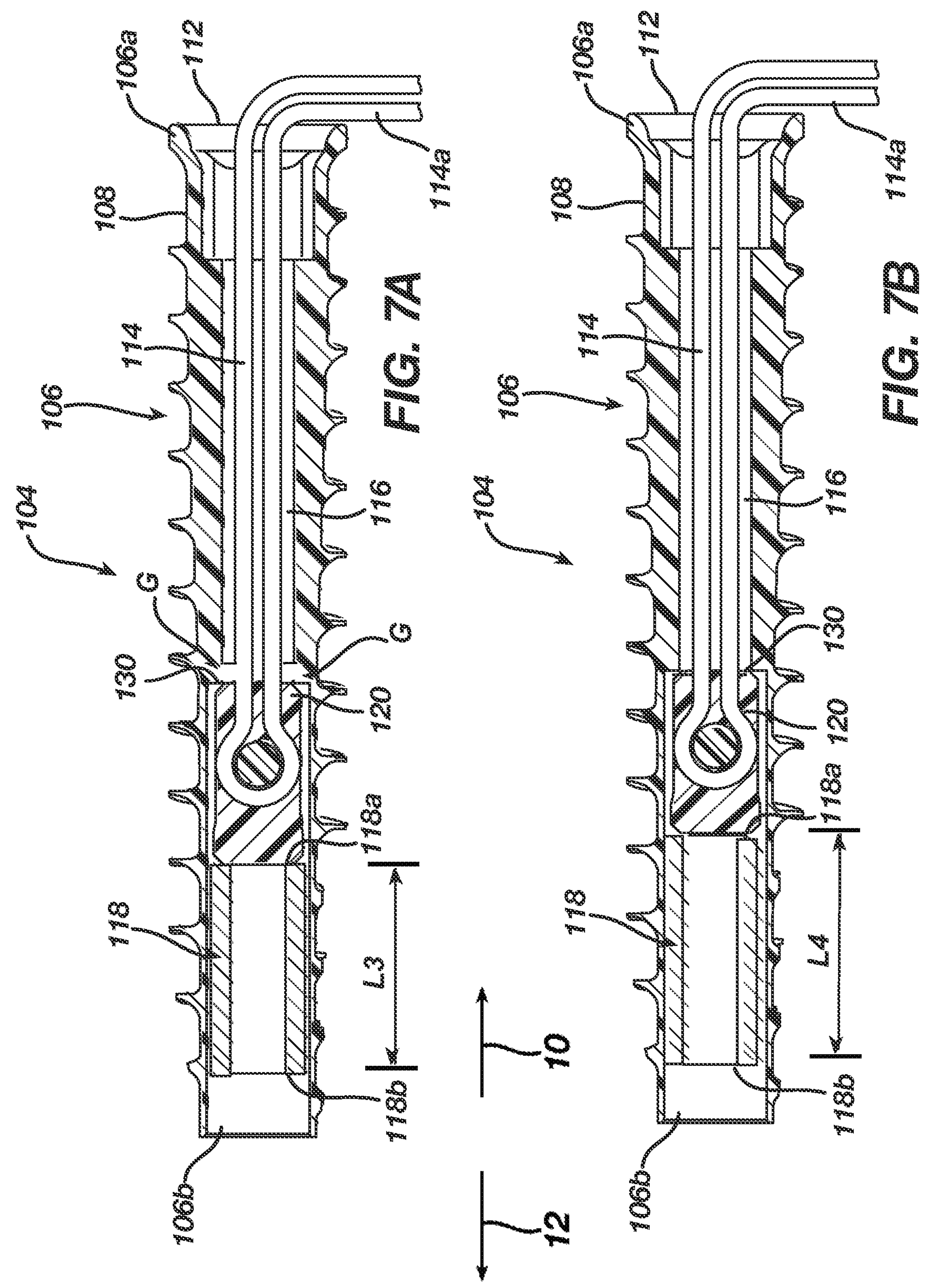
FIG. 7A is a cross-sectional view of another example first bone anchor for continuous compression and fixation between bones and/or soft tissue, the first bone anchor in a first state, according to aspects of the present invention.
FIG. 7B is a cross-sectional view of the example first bone anchor in FIG. 7A in a second state, according to aspects of the present invention.

Alternatively, in some embodiments, as particularly shown in FIGS. 7A and 7B (further discussed below), the resilient element 118 may be disposed in a distal direction 12 in relation to the suture coupler 120, and may be configured to elongate in response to the force in the proximal direction 10 on the suture coupler 120. In some embodiments, the outer body 106 may include a gap G between the inner channel 116 and the notch 130. Gap G may be configured such that when the resilient element 118 is at rest, the suture coupler 120 may be positioned at its distal most position (FIG. 7A). When the suture 114 is then pulled, the gap G may be closed as the suture coupler 120 moves proximally (FIG. 7B). The notch 130 prevents the suture coupler 120 from moving too far proximally and putting too much strain on the resilient element 118 or the connection of the suture coupler 120 to the resilient element 118. If the suture coupler 120 were to detach from the resilient element 118, the notch 130 would retain the suture coupler 120 in the first anchor 104.

In some embodiments, as particularly shown in FIGS. 7A and 7B, a length L3 (FIG. 7A) or L4 (FIG. 7B) of the resilient element 118 may be between the first end 118*a* and the second end 118*b* and may be configured to deform in response to the force on the suture coupler 120. As shown in FIG. 7B, a force on the suture coupler 120 in a proximal direction 10 (e.g., by pulling on suture 114), results in deformation of the resilient element 118 to the second state, where the resilient element 118 has a length L4. As shown in FIG. 7A, proximal translation of the suture coupler 120 in relation to the outer body 106 and a release of the force results in a return of the resilient element 118 to the first state, where the resilient element 118 has a length L3, and distal translation of the suture coupler 120. In some embodiments, as shown in FIGS. 7A and 7B, length L3 of resilient element 118 while in the first state (FIG. 7A) is shorter than L4 of resilient element 118 while in the second state (FIG. 7B). In some embodiments, the inner channel 116 may include an internal notch 130 configured to prevent the suture coupler 120 from moving proximally within the first bone anchor 104. Such configurations may provide for dynamic compression and/or decompression, for example, as a patient moves, the ability of a user (e.g., a surgeon) to set a correct or appropriate amount of tension across the anatomy (e.g., bone(s) and/or tissue), and/or continuous compression such that, for example, when the applicable anatomy gains laxity, the resilient element 118 may allow the suture 114 to gain compression.

In some embodiments, the resilient element 118 may include rubber, polyurethane, and/or nitinol. In some embodiments, the resilient element 118 may include a coil spring.

Figure 8:
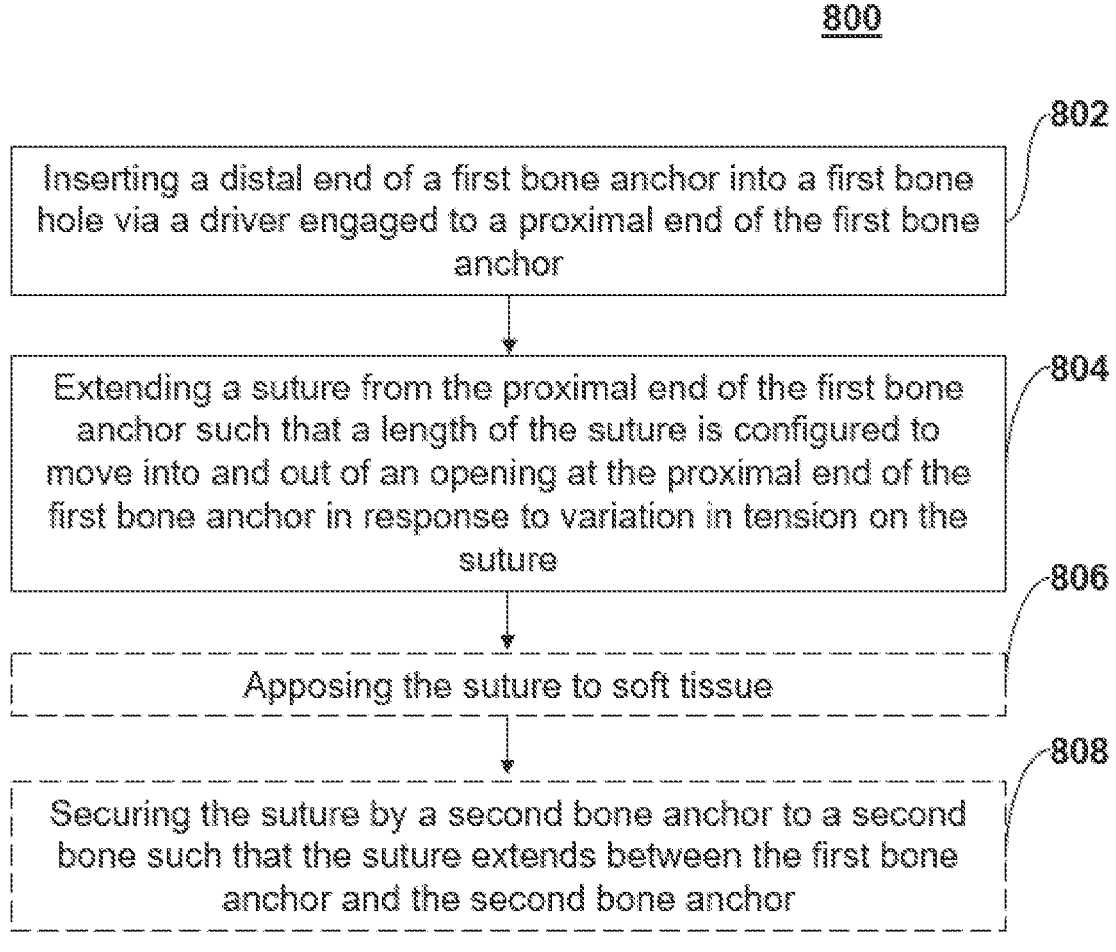
FIG. 8 is a flowchart of a method for bracing soft tissue according to aspects of the present invention.

FIG. 8 provides a flowchart of an example method of bracing soft tissue.

In block 802, the method may include inserting a distal end 104*b* of a first bone anchor 104 into a first bone hole 110*a* via a driver engaged to a proximal end 104*a* of the first bone anchor 104. This step may include rotating the driver to thereby rotate the first bone anchor 104 so that the first bone anchor 104 screws distally into the first bone hole 110*a*.

In block 804, the method may include extending a suture 114 from the proximal end 104*a* of the first bone anchor 104 such that a length of the suture 114 is configured to move into and out of an opening 112 at the proximal end 104*a* of the first bone anchor 104 in response to variation in tension on the suture 114.

In optional block 806, the method may include apposing the suture 114 to soft tissue.

In optional block 808, the method may include securing the suture 114 by a second bone anchor 122 to a second bone 124 such that the suture 114 extends between the first bone anchor 104 and the second bone anchor 122. Securing the suture 114 by the second bone anchor 122 to the second bone 124 may include securing the suture 114 such that it extends orthogonal to the first bone anchor 104.

The descriptions contained herein are examples of embodiments of the invention and are not intended in any way to limit the scope of the invention. As described herein, the invention contemplates many variations and modifications of structures and methods, including alternative materials, alternative configurations of component parts, and alternative method steps. Modifications and variations apparent to those having skill in the pertinent art according to the teachings of this disclosure are intended to be within the scope of the claims which follow.

The disclosed technology described herein can be further understood according to the following clauses.

Clause 1. An implant comprising: a first bone anchor comprising: an outer body comprising an outer surface configured to engage a first bone, an opening at a proximal end of the outer body configured to pass a suture therethrough, and an inner channel, a resilient element disposed within the inner channel of the outer body and being deformable between a first state and a second state, and a suture coupler disposed within the inner channel of the outer body, configured to couple to the suture, and engage to the resilient element such that a force on the suture coupler in a proximal direction results in deformation of the resilient element to the second state and proximal translation of the suture coupler in relation to the outer body and a release of the force results in a return of the resilient element to the first state and distal translation of the suture coupler.

Clause 2. The implant of clause 1, wherein the resilient element is disposed in a proximal direction in relation to the suture coupler and is configured to compress in response to the force in the proximal direction on the suture coupler.

Clause 3. The implant of clause 1, wherein the resilient element is disposed in a distal direction in relation to the suture coupler and is configured to elongate in response to the force in the proximal direction on the suture coupler.

Clause 4. The implant of clause 1, wherein the outer surface of the outer body comprises screw threads.

Clause 5. The implant of clause 1, wherein the proximal end of the outer body is shaped to receive a drive end of a suture anchor driver.

Clause 6. The implant of clause 1, further comprising: the suture, wherein tension on the suture is configured to apply the force on the suture coupler in the proximal direction.

Clause 7. The implant of clause 6, further comprising: a second bone anchor configured to engage the suture, wherein the first and second bone anchors are configured to engage one or more bones such that the suture extends orthogonally in relation to the first bone anchor.

Clause 8. The implant of clause 7, wherein the suture is configured appose soft tissue.

Clause 9. The implant of clause 7, wherein the second bone anchor comprises one or more of a threaded screw, a barbed fastener, a button, a cap, or combinations thereof.

Clause 10. The implant of clause 1, wherein a first end of the resilient element is prevented, by the outer body, from translating longitudinally in relation to the outer body, a second end of the resilient element is engaged to the suture coupler, and a length of the resilient element between the first end and the second end is configured to deform in response to the force on the suture coupler.

Clause 11. The implant of clause 10, wherein the inner channel comprises an internal notch configured to prevent the first end of the resilient element from moving proximally within the first bone anchor.

Clause 12. The implant of clause 1, wherein the resilient element comprises one or more of rubber, polyurethane, nitinol, or combinations thereof.

Clause 13. The implant of clause 1, wherein the resilient element comprises a coil spring.

Clause 14. A method of bracing soft tissue, the method comprising: inserting a distal end of a first bone anchor into a first bone hole via a driver engaged to a proximal end of the first bone anchor; and extending a suture from the proximal end of the first bone anchor such that a length of the suture is configured to move into and out of an opening at the proximal end of the first bone anchor in response to variation in tension on the suture.

Clause 15. The method of clause 14, further comprising: apposing the suture to soft tissue.

Clause 16. The method of clause 14, further comprising: securing the suture by a second bone anchor to a second bone such that the suture extends between the first bone anchor and the second bone anchor.

Clause 17. The method of clause 16, wherein securing the suture by the second bone anchor to the second bone comprises securing the suture such that it extends orthogonal to the first bone anchor.

Clause 18. The method of clause 14, wherein inserting the distal end of the first bone anchor into the first bone hole via the driver engaged to the proximal end of the first bone anchor comprises rotating the driver to thereby rotate the first bone anchor so that the first bone anchor screws distally into the first bone hole.

Clause 19. The method of clause 14, wherein the first bone anchor further comprises: an outer body comprising an outer surface configured to engage the first bone and an inner channel, a resilient element disposed within the inner channel of the outer body and being deformable between a first state and a second state, and a suture coupler disposed within the inner channel of the outer body, configured to couple to the suture, and engage to the resilient element such that tension in the suture applies a force on the suture coupler in a proximal direction, such that the force results in deformation of the resilient element to the second state and proximal translation of the suture coupler in relation to the outer body, and such that a release of the force results in a return of the resilient element to the first state and distal translation of the suture coupler.

Clause 20. The method of clause 19, wherein the resilient element comprises one or more of rubber, polyurethane, nitinol, or combinations thereof.

What is claimed is:

1. An implant comprising:

a suture; and a first bone anchor comprising:

an outer body comprising an outer surface configured to engage a first bone, an opening at a proximal end of the outer body configured to pass the suture therethrough, and an inner channel, wherein a distal-most end of the suture is disposed within the inner channel, a resilient element disposed within the inner channel of the outer body and being deformable between a first state and a second state, and a suture coupler disposed within the inner channel of the outer body, the suture coupler configured to couple to the suture, and engage to the resilient element such that a force on the suture coupler in a proximal direction results in deformation of the resilient element to the second state and proximal translation of the suture coupler in relation to the outer body and a release of the force results in a return of the resilient element to the first state and distal translation of the suture coupler, wherein the resilient element is disposed (i) proximal to a proximal-most end of the suture coupler, or (ii) distal to a distal-most end of the suture coupler.

2. The implant of claim 1, wherein the resilient element is disposed proximal to the proximal-most end of the suture coupler and is configured to compress in response to the force in the proximal direction on the suture coupler.

3. The implant of claim 1, wherein the resilient element is disposed distal to the distal-most end of the suture coupler and is configured to elongate in response to the force in the proximal direction on the suture coupler.

4. The implant of claim 1, wherein the outer surface of the outer body comprises screw threads.

5. The implant of claim 1, wherein the proximal end of the outer body is shaped to receive a drive end of a suture anchor driver.

6. The implant of claim 1, wherein tension on the suture is configured to apply the force on the suture coupler in the proximal direction.

7. The implant of claim 6, further comprising:

a second bone anchor configured to engage the suture, wherein the first and second bone anchors are configured to engage one or more bones such that the suture extends orthogonally in relation to the first bone anchor.

8. The implant of claim 7, wherein the suture is configured appose soft tissue.

9. The implant of claim 7, wherein the second bone anchor comprises one or more of a threaded screw, a barbed fastener, a button, a cap, or combinations thereof.

10. The implant of claim 1, wherein a first end of the resilient element is prevented, by the outer body, from translating longitudinally in relation to the outer body, a second end of the resilient element is engaged to the suture coupler, and a length of the resilient element between the first end and the second end is configured to deform in response to the force on the suture coupler.

11. The implant of claim 10, wherein the inner channel comprises an internal notch configured to prevent the first end of the resilient element from moving proximally within the first bone anchor.

12. The implant of claim 1, wherein the resilient element comprises one or more of rubber, polyurethane, nitinol, or combinations thereof.

13. The implant of claim 1, wherein the resilient element comprises a coil spring.

14. The implant of claim 1, wherein the suture is disposed within the inner channel of the outer body and within the resilient element.

15. The implant of claim 14, wherein the suture extends between and beyond distal and proximal ends of the resilient element.

16. A method of bracing soft tissue, the method comprising:

inserting a distal end of the outer body of the first bone anchor of claim 1 into a first bone hole via a driver engaged to the proximal end of the outer body of the first bone anchor; and extending the suture from the proximal end of the outer body of the first bone anchor such that a length of the suture is configured to move into and out of the opening at the proximal end of the outer body of the first bone anchor in response to variation in tension on the suture.

17. The method of claim 16, further comprising:

apposing the suture to soft tissue.

18. The method of claim 16, further comprising:

securing the suture by a second bone anchor to a second bone such that the suture extends between the first bone anchor and the second bone anchor.

19. The method of claim 18, wherein securing the suture by the second bone anchor to the second bone comprises securing the suture such that it extends orthogonal to the first bone anchor.

20. The method of claim 16, wherein inserting the distal end of the outer body of the first bone anchor into the first bone hole via the driver engaged to the proximal end of the outer body of the first bone anchor comprises rotating the driver to thereby rotate the first bone anchor so that the first bone anchor screws distally into the first bone hole.

* * * * *